United States Patent [19]

Fahmy

[11] Patent Number: 5,074,865

[45] Date of Patent: Dec. 24, 1991

[54] DISTRACTION APPARATUS FOR MAINTAINING FRACTURED JOINT ORIENTATION

[76] Inventor: Nabil R. Fahmy, The White House, Billy's Lane, Cheadle Hulme, Cheshire. SK8 6HT, England

[21] Appl. No.: 555,467

[22] PCT Filed: Feb. 17, 1989

[86] PCT No.: PCT/GB89/00170

§ 371 Date: Aug. 17, 1990

§ 102(e) Date: Aug. 17, 1990

[87] PCT Pub. No.: WO89/07421

PCT Pub. Date: Aug. 24, 1989

[30] Foreign Application Priority Data

Feb. 17, 1988 [GB] United Kingdom ............... 8803680

[51] Int. Cl.5 .............................................. A61F 5/04
[52] U.S. Cl. ..................................... 606/54; 606/57; 606/59; 606/105
[58] Field of Search ................... 606/54–55, 606/57–59, 72–73, 90, 105; 128/69

[56] References Cited

U.S. PATENT DOCUMENTS 4,869,242  9/1989  Galluzzo ........................ 606/59

FOREIGN PATENT DOCUMENTS 897232  1/1982  U.S.S.R. ............................ 606/57
1102585  7/1984  U.S.S.R. ........................... 606/105

OTHER PUBLICATIONS

"Biomechanics of Fracture Healing", Journal of Bone and Joint Surgery, p. 1049, vol. 37A#5, Oct. 1955.

Primary Examiner—Richard J. Apley
Assistant Examiner—Linda C. M. Dvorak
Attorney, Agent, or Firm—Nies, Kurz, Bergert & Tamburro

[57] ABSTRACT

Distraction apparatus for maintaining fractured joints during healing, comprising a pair of pins (10) for insertion into bone at positions proximal to and distal to an injured joint, and a pair of stainless steel wire springs (15) which are adjustably attached to the pins to determine and resiliently maintain the relative spacing of the pin insertions into the bone thus to retain the components of the joint during the healing process.

8 Claims, 3 Drawing Sheets

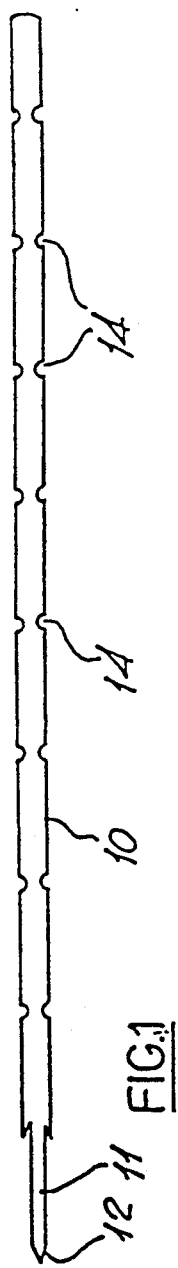
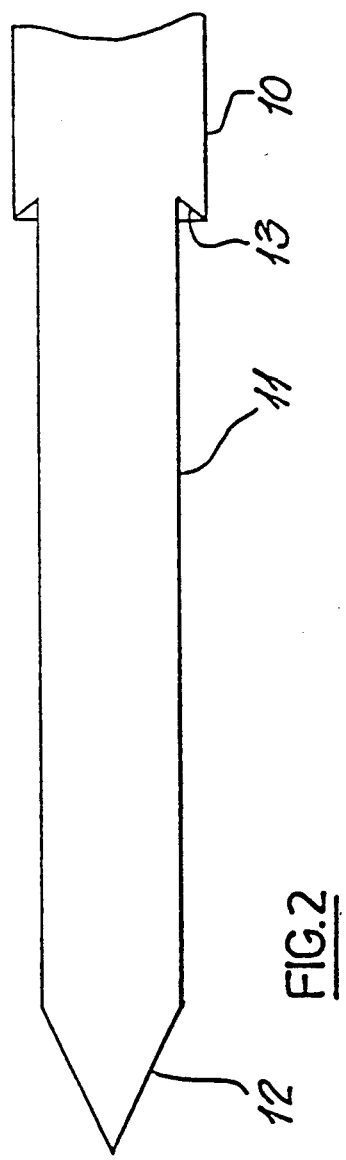
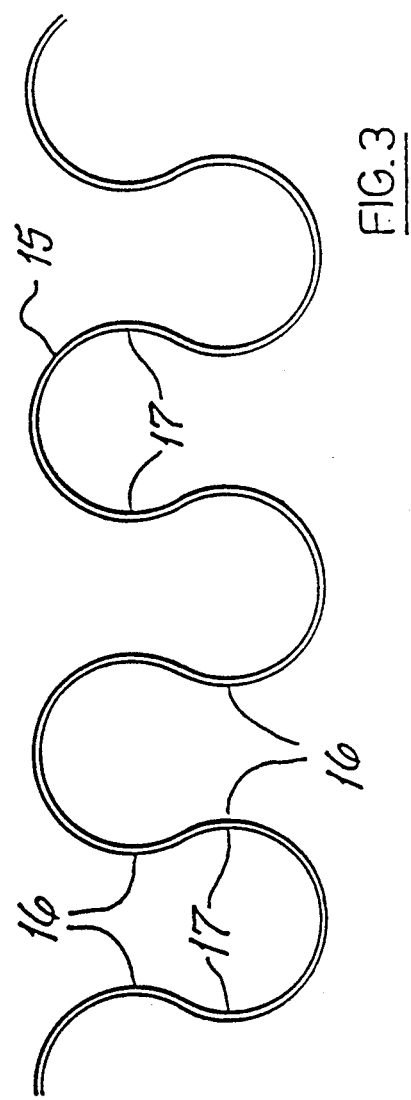

DISTRACTION APPARATUS FOR MAINTAINING FRACTURED JOINT ORIENTATION

This invention relates to distraction apparatus for maintaining fractured joints during healing and has a principal, though by no means exclusive, application in the treatment of intra-articular fracture dislocations of the joints of the hand. Joint injuries often result in displacement of the internal components of the joint and of bone fragments which have become fractured and dislocated in the injury.

In the treatment of such injuries it is often required to create traction across a joint so that the components therof are retained in appropriate relative dispositions during the healing process. However, it is also advantageous in certain cases to permit gentle controlled movement of the joint which helps to mould the irregular surfaces and prevents eventual stiffness.

An object of the present invention is to provide a distraction apparatus for intra-articular phalangeal and metacarpo-phalangeal fractures, which is easy to apply with reduced operative time, is versatile to the extent that the degree of distraction may be easily changed during the healing process, and which allows slight movement at the site.

According to the present invention, there is provided distraction apparatus for maintaining fractured joints during healing, comprising at least two pins having parts for insertion into bone, one proximal to and the other distal to the injured site, with the remainder of the length of the pins projecting externally and generally normal to the axis through the site, and resilient means to determine and resiliently maintain the relative spacing of the inserted parts of the pins, thus to retain the components of the joint; characterised by a pair of resilient connecting members adapted for attachment externally and directly to and between the pins at spaced positions thereon.

Embodiments of the invention will now be described, by way of example only, with reference to the accompanying drawings in which:

FIG. 1 illustrates a pin forming part of the apparatus;

FIG. 2 is an enlarged view of one end of the pin shown in FIG. 1.

FIG. 3 is a similarly enlarged view of part of a connecting member forming part of the apparatus;

Figure 4:
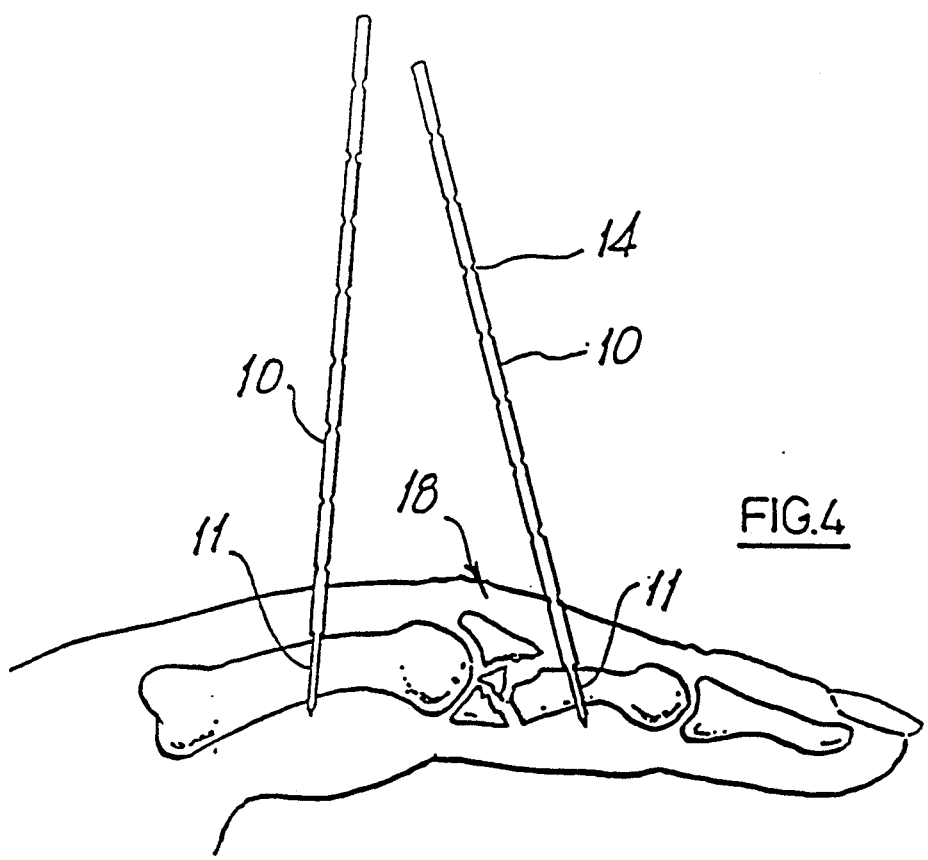
Figure 5:
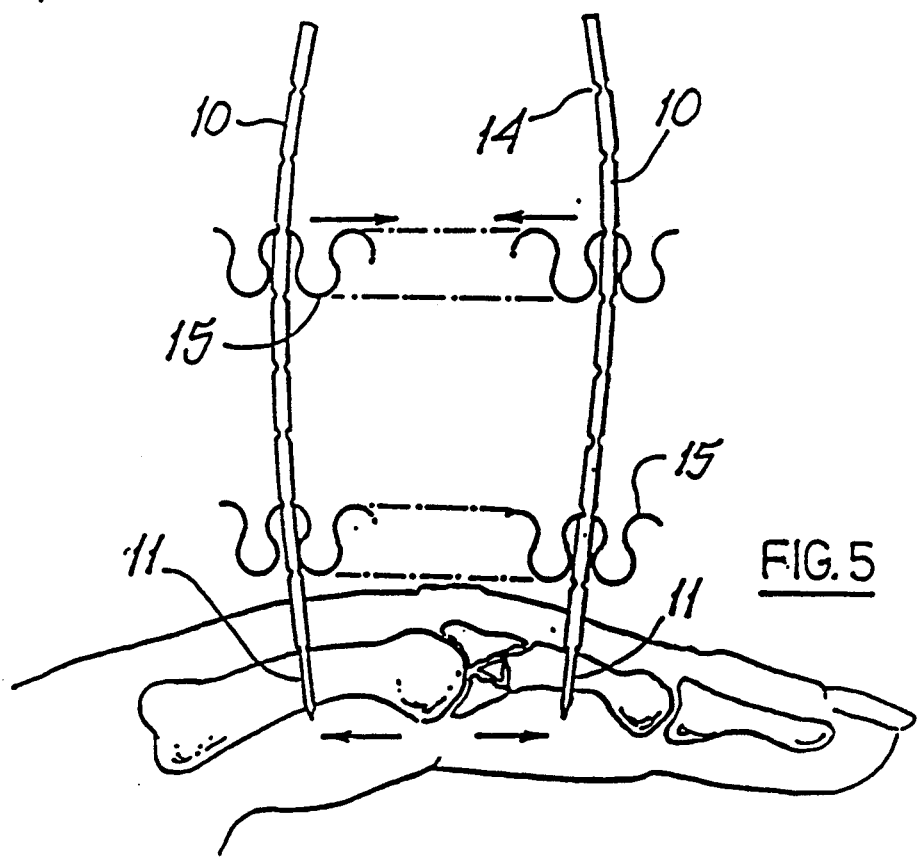
Figure 6:
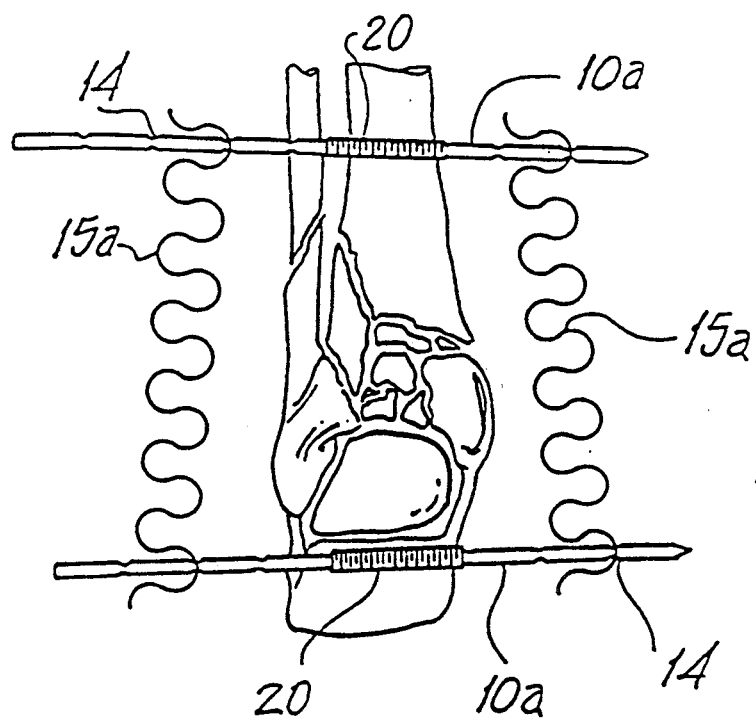
Figure 7:
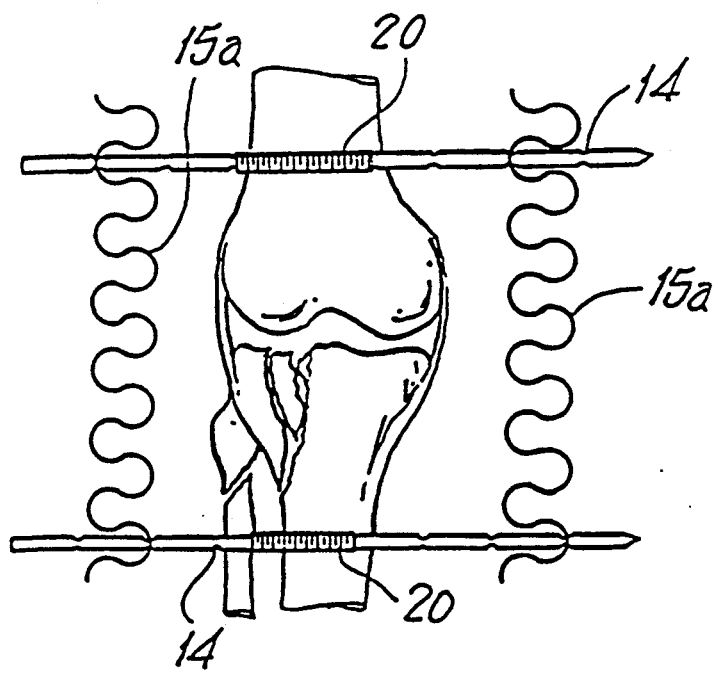

FIGS. 4 and 5 diagrammatically illustrate how the apparatus is applied to a finger joint; and FIGS. 6 and 7 similarly illustrate how a modified form of the apparatus may be applied to an ankle injury and a tibial plateau injury respectively.

Referring to FIGS. 1 to 3, the apparatus essentially comprises a pair of highly purified stainless steel pins 10, some 98 mm in length and with a major part of its length approximately 2 mm in diameter. As can be seen particularly in FIG. 2, in one end region 11 of each pin its diameter is reduced to 1.5 mm over a length of some 10 mm from a tapered or conical end 12.

An undercut annular shoulder 13 is provided at the position spaced from the end 12 where the diameter of the pin 10 is reduced.

As will be described in relation to FIGS. 4 and 5, the length of the reduced diameter portion 11 will be selected according to the required depth of bone penetration, and the shoulder 13 prevents the pin from passing further through the bone.

Along the remaining length of each pin 10 at 1 cm intervals, its diameter is reduced by grooves 14 of approximately 0.5 mm depth.

FIG. 3 illustrates part of one of a pair of stainless steel wire springs 15 shaped in a serpentine manner presenting alternate narrow and wide sections 16 and 17 of 1.5 mm and 2.5 mm width respectively. Each spring 15 has some 8 turns throughout its length, and of the pair of springs provided in the apparatus one will be of a wire 1 mm in diameter whilst the other will be smaller at approximately 0.7 mm in diameter.

Referring now to FIGS. 4 and 5 the apparatus is applied, in this example to a fractured finger joint, by initially inserting the ends 12 of pins 10 into and through the bone, proximally and distally respectively to the injury site 18. In the example shown the reduced diameter portions 11 of the two pins are of different lengths so as to project fully through two different thicknesses of bone without extending beyond it.

The insertion of the pins will take place under general or regional anaesthesia, and then while traction is applied to the finger the thicker of the two springs 15 is attached to and between the pins 10, its position therealong being determined by location in the first or second grooves 14 close to the finger. This has the effect of moving the free ends of the pins apart, and subsequently the second and more resilient of the two springs 15 is applied so as to urge the free ends of the pins together to a controlled extent to effect the desired amount of distraction of the joint. The degree of distraction can be initially fixed and subsequently altered easily by moving the two springs closer or spacing them further along the wires, or by adjusting the number of turns of one or both springs between the pins. The final position may be checked by X-ray, and once the components of the fractured joint are held in proper inter-relationship, a sterile padded dressing may be applied to the injured finger. The springs 15 may be secured by adding a small amount of mixed fast setting polymer and monomer where the springs are attached to the pins, and the excess lengths of wire and springs may be removed by cutting so that the padded dressing may enclose the entire apparatus. The apparatus is light in weight and of minimal hinderance so that the patient may continue normal activities and may be seen by the practitioner at regular intervals when further X-rays inspections may be made to determine the progress of the treatment. Once the joint is healed the springs and pins are removed leaving the healed joint in a self-supporting mode.

The distraction apparatus herein described can be used in excision arthroplasty of the proximal interphalangeal or the metacarpo-phalangeal joints, so long as the collateral ligaments are not disrupted. It may be used in cases of phalangeal fractures or metacarpal fractures by using gentle distraction initially to maintain reduction for a suitable period to be followed by gentle compression until bony union is achieved.

By suitably increasing the scale of the parts of the apparatus, it may be applied to other intra-articular fractures such as those illustrated in FIGS. 6 and 7, e.g. comminuted fracture of the distal end of the radius, distal end of the tibia or of the tibial plateau. In these cases, the pins 10a, for location, may be threaded centrally as illustrated at 20, and extend through the site to receive springs 15a between respective adjacent grooved end regions of the two pins. In this embodiment, the diameters of pins 10a are constant (except for the grooves 14) at least between the base of the conical end and the far end of the threaded part 20.

I claim:

1. Distraction apparatus for maintaining fractured joints during healing, comprising at least two pins having parts for insertion into bone, one on each side of the injured site, with the remainder of the length of the pins projecting externally and generally normal to the axis through the site, and resilient means to determine and resiliently maintain the relative spacing of the inserted parts of the pins, thus to retain the components of the joint; characterized by a pair of resilient connecting members both adapted for attachment externally and directly to and between the pins and both adjustable in position longitudinally along the lengths of the pins, said pins having means to accommodate the attachment of the resilient connecting members to said pins.

2. Distraction apparatus according to claim 1, wherein each said pin comprises a major part of its length of a first diameter, and a shorter part close to a conical or tapered end, of a reduced diameter, with an annular shoulder between said two parts to determine the extent of insertion of the pin in the bone during application.

3. Distraction apparatus according to claim 2, wherein said annular shoulder is undercut.

4. Distraction apparatus according to any of claims 1 to claim 3, wherein each said pin has, in its major part, longitudinally spaced circumferential grooves for location of the connecting members.

5. Distraction apparatus according to claim 1, wherein at least one of the resilient connecting members comprises a stainless steel wire spring, shaped in a serpentine manner.

6. Distraction apparatus according to claim 1, wherein said resilient connecting members are both constructed as stainless steel wire springs shaped in a serpentine manner, one being of greater resilience than the other.

7. Distraction apparatus according to claim 1, wherein each pin is threaded part way along its length.

8. Distraction apparatus according to claim 7, wherein each pin has a central threaded portion with non-threaded portions extending therefrom to the two ends, and circumferential grooves for location of connecting members to the non-threaded portions.

* * * * *